(12) United States Patent
Castro (10) Patent No.: US 12,036,131 B2
(45) Date of Patent: Jul. 16, 2024

(54) JOINT IMPLANT (71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 324 days.

(21) Appl. No.: 16/964,626

(22) PCT Filed: Mar. 6, 2020

(86) PCT No.: PCT/US2020/021304
§ 371 (c)(1),
(2) Date: Jul. 24, 2020

(87) PCT Pub. No.: WO2020/242551
PCT Pub. Date: Dec. 3, 2020

(65) Prior Publication Data
US 2023/0201004 A1 Jun. 29, 2023

(51) Int. Cl.
A61F 2/44 (2006.01)
A61F 2/30 (2006.01)
A61F 2/46 (2006.01)

(52) U.S. Cl.
CPC .......... *A61F 2/447* (2013.01); *A61F 2/30771* (2013.01); *A61F 2/4618* (2013.01); *A61F 2/4644* (2013.01); A61F 2002/30158 (2013.01); A61F 2002/30579 (2013.01); A61F 2002/30845 (2013.01); A61F 2002/4619 (2013.01); A61F 2002/4627 (2013.01); A61F 2002/4645 (2013.01)

(58) Field of Classification Search
CPC .......... A61F 2/44; A61F 2/447; A61F 2/4618; A61F 2/4644; A61F 2/30771; A61F 2002/30158; A61F 2002/30579; A61F 2002/30845; A61F 2002/4619; A61F 2002/4627; A61F 2002/4645
USPC .................. 623/17.11–17.16; 606/99–100
See application file for complete search history.

(56) References Cited

U.S. PATENT DOCUMENTS

| | | |
|---|---|---|
| 6,770,096 B2 | 8/2004 | Bolger et al. |
| 6,824,564 B2 | 11/2004 | Crozet |
| 6,981,975 B2 | 1/2006 | Michelson |
| 7,594,932 B2* | 9/2009 | Aferzon ............... A61F 2/4611 623/17.16 |
| 8,366,774 B1 | 2/2013 | Bruffey et al. |
| 8,382,843 B2 | 2/2013 | Laurence et al. |
| 8,968,405 B2* | 3/2015 | Kirwan ................. A61F 2/447 623/17.11 |
| 9,539,110 B2 | 1/2017 | Bergey |

(Continued)

FOREIGN PATENT DOCUMENTS

| | | |
|---|---|---|
| WO | WO 2007/079021 | 7/2007 |
| WO | 2019/018014 | 1/2019 |

*Primary Examiner* — Jessica Weiss
(74) *Attorney, Agent, or Firm* — BUSINESS PATENT LAW, PLLC (57) ABSTRACT A joint implant adapted for use in joint surgeries. Among other things, the joint implant has an anterior cutting edge and a rotatable cutter supported by a rotatable shaft. When surgical parameters require, the shaft can be detached from the implant. The present implant can include a rotatable shaft that has a conduit and windows.

25 Claims, 4 Drawing Sheets (56) References Cited

U.S. PATENT DOCUMENTS

| | | | |
|---|---|---|---|
| 2003/0187436 A1* | 10/2003 | Bolger | A61B 17/7077 606/279 |
| 2006/0235520 A1* | 10/2006 | Pannu | A61B 17/025 606/90 |
| 2007/0118220 A1 | 5/2007 | Liu | |
| 2007/0270961 A1 | 11/2007 | Ferguson | |
| 2008/0027550 A1 | 1/2008 | Link et al. | |
| 2008/0132949 A1* | 6/2008 | Aferzon | A61F 2/446 606/246 |
| 2010/0185289 A1* | 7/2010 | Kirwan | A61F 2/447 623/17.11 |
| 2011/0035007 A1* | 2/2011 | Patel | A61F 2/4465 623/17.11 |
| 2012/0277868 A1* | 11/2012 | Walters | A61F 2/447 623/17.16 |
| 2013/0268076 A1* | 10/2013 | Carlson | A61F 2/442 623/17.16 |
| 2014/0094918 A1* | 4/2014 | Vishnubholta | A61F 2/442 623/17.16 |
| 2014/0114421 A1* | 4/2014 | Ullrich, Jr. | A61F 2/4465 623/17.16 |
| 2014/0121773 A1 | 5/2014 | Patel et al. | |
| 2015/0265416 A1* | 9/2015 | Aferzon | A61F 2/446 623/17.16 |
| 2016/0374831 A1 | 12/2016 | Duffield et al. | |
| 2017/0095352 A1* | 4/2017 | Bruffey | A61F 2/442 |
| 2019/0314171 A1* | 10/2019 | Castro | A61B 17/7032 |
| 2020/0179135 A1* | 6/2020 | Castro | A61F 2/447 |

\* cited by examiner

JOINT IMPLANT

PRIORITY

Applicant claims priority to PCT US2020/021304—Joint Implant—filed on Mar. 6, 2020 that claims the benefit of U.S. Provisional Application No. 62/852,401—Joint Implant—filed on May 24, 2019.

BACKGROUND OF THE INVENTION

A. Field of the Invention

The present invention is a joint implant. Among other things, the implant of the current system has a cutting edge as well as a rotatable cutter. Select preferred embodiments of the current implant can be provided with a socket and bearing that allow a rotatable shaft to be detached/reattached from the socket. Other preferred embodiments of the present implant include a rotatable shaft that has a conduit and windows.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 6,770,096—Bolger, et al. that discloses an interbody spinal stabilization cage and spinal stabilization method; 2) U.S. Pat. No. 6,824,564—Crozet that discloses a two-part intersomatic implant; 3) U.S. Pat. No. 6,981,975—Michelson that discloses a method for inserting a spinal fusion implant having deployable bone engaging projections; 4) U.S. Pat. No. 7,594,932—Aferzon, et al. discloses an apparatus for anterior intervertebral spinal fixation and fusion; 5) U.S. Pat. No. 8,366,774—Bruffey, et al. that discloses an apparatus for anterior intervertebral spinal fixation and fusion; 6) U.S. Pat. No. 8,382,843—Laurence, et al. that discloses an intervertebral implant with blades for connecting to adjacent vertebral bodies; 7) U.S. Pat. No. 9,539,110—Bergey that discloses an interbody prosthetic device with compound-arc, blade anchor; 8) US Published Patent Application No. 20030187435—Bolger, et al. that an interbody spinal stabilization cage and spinal stabilization method; 9) US Published Patent Application 2007011820—Liu, et al. that discloses a vertebral implant for promoting arthrodesis of the spine; 10) US Published Patent Application No. 20070270961—Ferguson that discloses a spinal implant deployable with retractable barbs; 11) US Published Patent Application No. 20080027550—Link, et al. that discloses a cervical intervertebral disc prosthesis comprising an anti-dislocation device and instruments; 12) US Published Patent Application No. 20140094918—Vishnubholta, et al. that discloses a stand-alone interbody fixation system; 13) US Published Patent Application No. 20140114421—Titan Spine, LLC that discloses an interbody spinal implant having a roughened surface topography; 14) US Published Patent Application No. 20140121773—Patel, et al. that discloses a stand-alone interbody fixation system; 15) US Published Patent Application No. 20150265416—Aferzon, et al. that discloses an apparatus for anterior intervertebral spinal fixation and fusion; 16) US Published Patent Application No. 20160374831—Duffield, et al. that discloses an interbody fusion device and system for implantation; and 17) WIPO Published Patent Application No. 2007/079021—Aferzon, et al. that discloses an apparatus for anterior intervertebral spinal fixation and fusion.

Among other things, none of the above listed references disclose a joint implant comprising a biocompatible construction with a longitudinal axis spanning a longer dimension of the biocompatible construction; the biocompatible construction comprising: a) openings outward from the longitudinal axis; b) an anterior side comprising: i) a cutting edge; and ii a socket; c) a surgeon facing side comprising a bearing; d) a rotatable shaft, extending along the longitudinal axis, engaging the socket and the bearing, wherein the rotatable shaft is detachable from the biocompatible construction; and e) first and second arms connected with the rotatable shaft; the first and second arms supporting first and second cutters comprising one or more blades, wherein on rotation of the shaft, the blades are adapted to cut in a clockwise or counterclockwise direction.

Among other things, none of the above listed references disclose a joint implant comprising a biocompatible construction with a longitudinal axis spanning a longer dimension of the biocompatible construction; the biocompatible construction comprising: a) a first trapezoidal surface comprising a first aperture therein and a first two margins of equal length; b) a second trapezoidal surface opposed from the first trapezoidal surface; the second trapezoidal surface comprising a second aperture therein and a second two margins of equal length; c) an anterior side extending between the trapezoidal surfaces; the anterior side comprising a cutting edge and an orifice extending through the anterior side and the cutting edge; d) a surgeon facing side comprising a bearing; the surgeon facing side extending between the trapezoidal surfaces; and e) a rotatable shaft extending from the orifice into the bearing; the rotatable shaft comprising: i) a conduit extending through a length of the rotatable shaft; the conduit defined by an inward face of the rotatable shaft's cylindrical wall; ii) one or more windows, positioned on the cylindrical wall; each window exposing the conduit to a surgically created cavity external from the joint implant; and iii) first and second arms connected with the rotatable shaft; the first and second arms supporting first and second cutters comprising one or more blades, wherein on rotation of the shaft, the blades are adapted to cut in a clockwise or counterclockwise direction.

SUMMARY OF THE INVENTION

The more tools or instruments inserted into a surgical field, the greater the possibility of an error resulting in patient injury. Due to the simplicity of the current joint implant, a number of surgical tools required and steps associated with performing prior state-of-the-art fusions can be eliminated. Among other things, use of the current invention allows arthrodesis procedures to be performed in the cervical spine, sacroiliac joint, ankle, hand or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current joint implant system can accomplish sacroiliac fusions through either a posterior or lateral approach with fewer surgical tools and steps.

Unlike other joint implants, the present joint implant includes a cutting edge and one or more rotatable cutters including one or more blades connected to a rotatable shaft. Among other things, it is believed that the cutters can assist with the postoperative stabilization of the joint implant. In accordance with the current invention, rotation of a blade about 90 degrees allows the blade to extend beyond the joint implant's construction and penetrate adjacent cartilage and bone. Select preferred embodiments of the current invention include a socket and bearing that allow the rotatable shaft to be detached/reattached from socket. Detachment/reattachment of the rotatable shaft allows the surgeon to move of the rotatable shaft along its longitudinal axis. Other embodiments of the present invention include a rotatable shaft with a conduit, windows, first and second arms connected to the rotatable shaft where the arms support cutters.

An aspect of the present invention is to provide a joint implant with an anterior side having a cutting edge.

Still another aspect of the present invention is to provide a joint implant with an anterior side including a socket.

It is yet another aspect of the present invention to provide an anterior side including an orifice.

Still another aspect of the present invention is to provide a joint implant with a rotatable shaft extending from the anterior side into the surgeon facing side.

It is still another aspect of the present invention to provide a joint implant with one or more rotatable cutters affixed to the shaft, where each cutter can include one or more blades.

Yet still another aspect of the present invention is to provide a joint implant where rotation of the rotatable cutter causes one or more of the cutters to extend beyond the biocompatible construction.

Still another aspect of the present invention is to provide a joint implant with rotatable cutters for cutting in the clockwise or counterclockwise directions.

Yet another aspect of the present invention is to provide a joint implant with a socket and bearing adapted to engage the rotatable shaft.

Yet still another aspect of the present invention is to provide a rotatable shaft including a conduit and one or more windows for delivery of biocompatible instruments, compositions or substances.

It is yet another aspect of the present invention is to provide a joint implant that, after insertion into the surgically created opening, provides distraction.

Still another aspect of the present invention is to provide a joint implant that after insertion into the posterior cervical facet joint, the distraction can indirectly provide some neuroforaminal decompression.

It is still another aspect of the present invention to provide a joint implant with a framework or biocompatible construction that can lessen any joint implant subsidence.

Yet another aspect of the present invention is to provide a joint implant that includes surface treatments. Surface treatments can improve fixation of the joint implant, and it is believed that when the joint implant is inserted at an angle perpendicular to the joint surfaces, surface treatments significantly improve fusion.

It is still another aspect of the present invention to provide a joint implant where the rotatable shaft can be detached from the joint implant without compromising the stability of the implant remaining in the surgically created cavity.

Still another aspect of the present invention is to provide edges on the cutting arms that can assist with the morselization of bone.

A preferred embodiment of the current invention can be described as a joint implant (100) comprising a biocompatible construction with a longitudinal axis (X-X) measured in a coexisting or parallel direction of a longest dimension of the biocompatible construction; the biocompatible construction comprising: a) openings (110) outward from the longitudinal axis (X-X); b) an anterior side (102) comprising: i) an outward cutting edge (300); and ii) an inward socket (330); c) a surgeon facing side (104), opposite the anterior side (102), comprising a bearing (180) comprising opposed first and second gaps (182F, 182S) perpendicular to the longitudinal axis (X-X); d) a rotatable shaft (240) engaging the socket and extending along the longitudinal axis (X-X) from the socket (330) through the bearing (180), wherein the rotatable shaft (240) is detachable from the socket (330) and the bearing (180); and e) first and second arms (262F, 262S) connected with the rotatable shaft (240); the first and second arms (262F, 262S) supporting first and second cutters (260F, 260S) comprising one or more blades (268F, 268S), wherein on rotation of the shaft (240), the blades (268F, 268S) are adapted to cut in a clockwise or counterclockwise direction.

Another preferred embodiment of the current invention can be described as a joint implant (100) comprising a biocompatible construction with a longitudinal axis (X-X) spanning a longest dimension of the biocompatible construction; the biocompatible construction comprising: a) openings (110) outward from the longitudinal axis (X-X); b) an anterior side (102) comprising: i) a cutting edge (300); and ii) an inward socket (330); c) a surgeon facing side (104) comprising a bearing (180) comprising first and second gaps (182F, 182S); d) a rotatable shaft (240), extending along or parallel to the longitudinal axis (X-X), engaging the socket (330) and the bearing (180), wherein the rotatable shaft (240) is detachable from the biocompatible construction; and e) first and second arms (262F, 262S) connected with the rotatable shaft (240); the first and second arms (262F, 262S) supporting first and second cutters (260F, 260S) comprising one or more blades (268F, 268S), wherein on rotation of the shaft (240), the blades (268F, 268S) are adapted to cut in a clockwise or counterclockwise direction.

Still another preferred embodiment of the current invention can be described as a joint implant (100) comprising a biocompatible construction with a longitudinal axis (X-X) spanning a longer dimension of the biocompatible construction; the biocompatible construction comprising: a) openings (110) outward from the longitudinal axis (X-X); b) an anterior side (102) comprising: i) a cutting edge (300); and ii) a socket (330); c) a surgeon facing side (104) comprising a bearing (180); d) a rotatable shaft (240), extending along the longitudinal axis (X-X), engaging the socket (330) and the bearing (180), wherein the rotatable shaft (240) is detachable from the biocompatible construction; and e) first and second arms (262F, 262S) connected with the rotatable shaft (240); the first and second arms (262F, 262S) supporting first and second cutters (260F, 260S) comprising one or more blades (268F, 268S), wherein on rotation of the shaft (240), the blades are adapted to cut in a clockwise or counterclockwise direction.

Yet another preferred embodiment of the current invention can be described as a joint implant (110) comprising a biocompatible construction with a longitudinal axis (X-X) spanning a longer dimension of the biocompatible construction; the biocompatible construction comprising: a) a first trapezoidal surface (450) comprising a first aperture (452) therein and a first two margins (454, 456) of equal length; b) a second trapezoidal surface (460) opposed from the first trapezoidal surface (460); the second trapezoidal surface comprising a second aperture (462) therein and a second two margins (464, 466) of equal length; c) an anterior side (102) extending between the trapezoidal surfaces (450, 460); the anterior side (102) comprising a cutting edge (300) and an orifice (470) extending through the anterior side (102) and the cutting edge (300); d) a surgeon facing side (104) comprising a bearing (180); the surgeon facing side (104) extending between the trapezoidal surfaces (450); and e) a rotatable shaft (240) extending from the orifice (470) into the bearing (180); the rotatable shaft (240) comprising: i) a conduit (242) extending through a length of the rotatable shaft (240); the conduit (242) defined by an inward face (246) of the rotatable shaft's cylindrical wall (244); ii) one or more windows (248), positioned on the cylindrical wall (244); each window (248) exposing the conduit (242) to a surgically created cavity external from the joint implant (100); and iii) first and second arms (262F, 262S) connected with the rotatable shaft (240); the first and second arms (262F, 262S) supporting first and second cutters (260F, 260S) comprising one or more blades (268F, 268S), wherein on rotation of the shaft (240), the blades (268F, 268S) are adapted to cut in a clockwise or counterclockwise direction.

It is the novel and unique interaction of these simple elements which creates the system within the ambit of the present invention. Pursuant to the Articles of the Patent Cooperation Treaty and/or Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention. As used herein, with respect to the joint implant: 1) "anterior" of the joint implant means the side of the implant most distant from the surgeon and 2) "posterior or surgeon-facing side" of the joint implant means the side of the implant nearest the surgeon.

In the most general sense, the present invention is a joint arthrodesis system where an implant is surgically inserted into or across a joint space. The current implant can be useful for surgeries that can assist in stabilizing injured, deformed and or degenerative joints. Preferred embodiments of the current invention can be employed with ankle, cervical, hand, sacroiliac or other orthopaedic procedures. It appears that the present system is particularly useful for posterior cervical fusions and sacroiliac joint fusions. However, the current invention can also be used to fuse the tibia to the talus, the talus to the calcaneus, and metacarpals to the phalanges.

Preferred embodiments of the current joint implants can be manufactured of titanium alloys, stainless steel, resorbable polymers, non-resorbable polymers or any other composition acceptable in the art. Meeting a long felt but unfilled need in the orthopaedic surgical arts, the novel and unique structures of the present combinations allow the surgical team to, among other things, simplify previous procedures.

The present invention has a cutting edge and a rotatable cutter including one or more blades. The cutting edge of the implant's biocompatible composition is capable of dissecting through adipose, muscle and/or joint capsule tissues. The rotatable cutter of the implant is capable of cutting cartilage and bone and can be associated with the creation of the surgical cavity. Further, the rotatable cutter can morselize bone in preparation for fusion. The combination of the cutting edge(s) and rotatable cutter of the current joint implant meet long felt but unfilled needs in the orthopedic surgical arts: among other things, these novel and unique structures allow the surgeon to simplify the previous operating procedures utilized for posterior cervical, sacroiliac, and other joint fusions.

Devices that insert biocompatible, osteogenic and/or other substances into the interior volume of the implant can be used with the present invention. The current joint implant is also compatible with flexible drills, fiber optics, vacuums, one or more cannulas and one or more devices for inserting the joint implant. Combinations of one or more of the before identified ancillary devices and the current joint implant can assist with the creation and healing of the surgical wound.

Openings of the current joint implant increase the probability of the osteogenic materials and/or arthrodesis accelerating substances procuring a blood supply. And it is believed that increasing the blood supply to the osteogenic materials held by the joint implant or implant increases the probability of successful fusion. Introduction of osteogenic and other substances into the implant can hasten the healing of the surgical wound.

Figure 1:
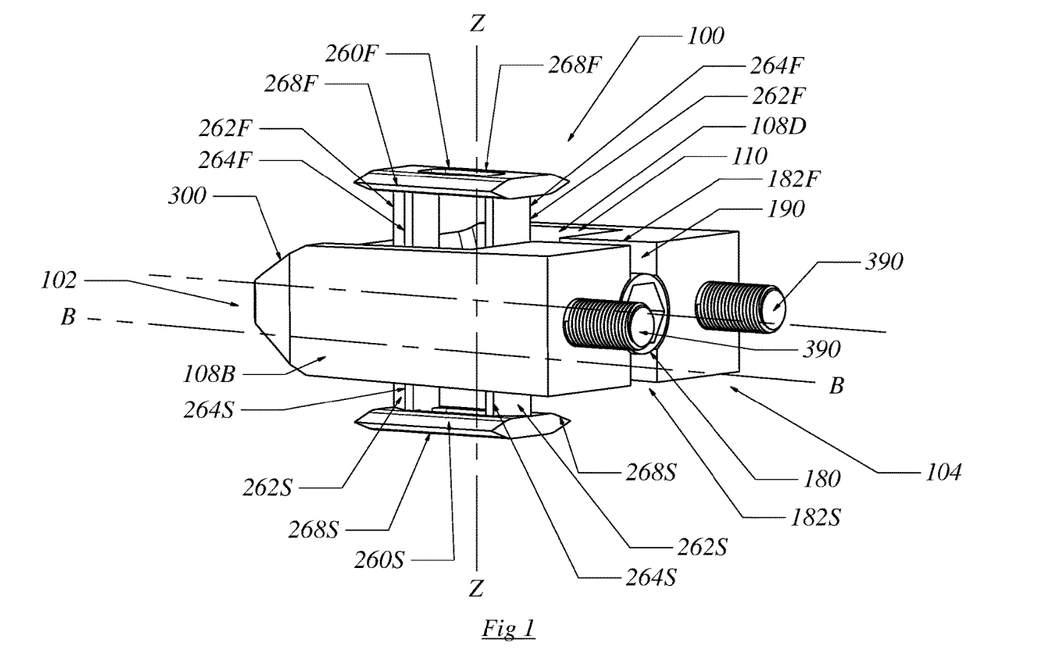
FIG. 1 is a perspective of a preferred embodiment of implant (100) where cutters (260F, 260S) extend beyond opening (110).
Figure 2:
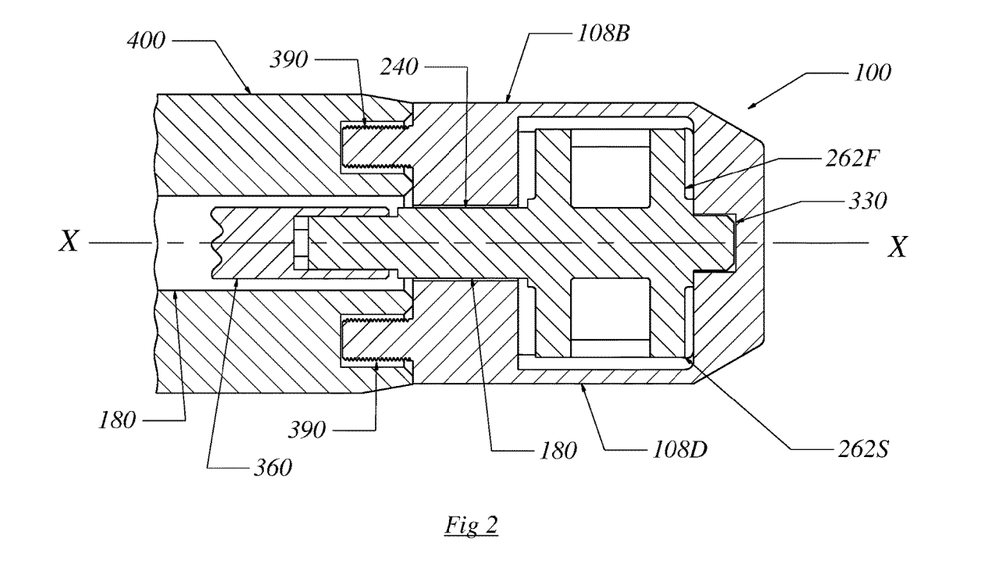
FIG. 2 is a top planar view of section B-B of FIG. 1, where cutters (260F, 260S) of implant (100) do not extend beyond opening (110).

With reference to FIGS. 1 and 2, a preferred embodiment of implant (100) is enabled. Implant (100) is provided with a biocompatible construction including a longitudinal axis X-X that can be measured in a coexisting or parallel direction of a longest dimension of the biocompatible construction. In selected preferred embodiments, when engineering parameters require, longitudinal axis X-X can be offset from center. Superior opening (110) and opposed inferior opening (not shown in FIG. 1) are positioned outward from implant's longitudinal axis X-X.

Implant (100) includes anterior side (102), posterior or surgeon facing side (104) and lateral sides (108B, 108D) extending between anterior side (102) and surgeon facing side (104). Anterior side (102) of implant (100) is provided with cutting edge (300) on the outward face of anterior side (102) and socket (330) on the inward face of anterior side (102). Surgeon facing side (104) is provided with a bearing (180) and at least one connector (390) adapted to engage an insertion device (400). In the FIGS. 1 and 2 preferred embodiment of implant (100), surgeon facing side (104) is provided with gaps (182F, 182S) creating pathway (190) through bearing (180) of posterior side (104).

As shown, rotatable shaft (240) extends along longitudinal axis X-X from anterior socket (330) through bearing (180). However, in other preferred embodiments, rotatable shaft (240) can contact bearing (180) without extending through bearing (180). Arms (262F, 262S) are connected to rotatable shaft (240) and support cutters (260F, 260S). Blades (268F, 268S) associated with cutters (260F, 260S) are adapted to cut when rotated in a clockwise or counterclockwise direction when shaft (240) is rotated. Sharp edges (264F, 264S) of arms (262F, 262S) can be adapted to remove cartilage, expose subcortical bone and/or morselize graft material. Tool (360) can be used to rotate shaft (240). In select preferred embodiments anterior side (102) is of lesser cross-sectional area than surgeon facing side (104).

Regarding the preferred embodiment of the current implant enabled in FIGS. 1 and 2, when surgical conditions require shaft (240) can be moved longitudinally along axis X-X and shaft (240) can be detached/reattached from socket (330). When medically required, rotation of shaft (240) positions arms (262F, 262S) such that shaft (240) can be detached from socket (330) and arms (262F, 262S) can be pulled through pathway (190).

With a view toward to FIGS. 1 and 2 and within the scope of the current invention, preferred embodiments of joint implant (100) can have a length greater than a width. In select preferred embodiments, the width of joint implant (100) is greater than the height of joint implant (100). In other preferred embodiments of joint implant (100), the height of implant (100) is greater than the width of joint implant (100). The inward sides of anterior side (102), posterior side (104) and lengthwise sides (108B and 108D) facing longitudinal axis X-X create an available inner volume of implant (100) which can receive osteogenic as well as other substances.

As measured along longitudinal axis X-X of implant's (100) biocompatible construction, preferred embodiments are provided with cutting edge (300) that can be up to about 3 millimeters in length. The length of implant (100), including cutting edge (300) can be from about 6 millimeters to about 50 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

With respect to this application and in view FIGS. 1 and 2, the longitudinal axis of joint implant (100) is measured along axis X-X. Axis X-X can correspond with shaft (240) or in some preferred embodiments, shaft (240) can be offset from axis X-X. Width of implant (100) is measured along axis Y-Y or an axis parallel to axis Y-Y shown in FIG. 1. Height of joint implant is measured along axis Z-Z or an axis parallel to axis Z-Z of the joint implant's biocompatible construction.

Figure 3:
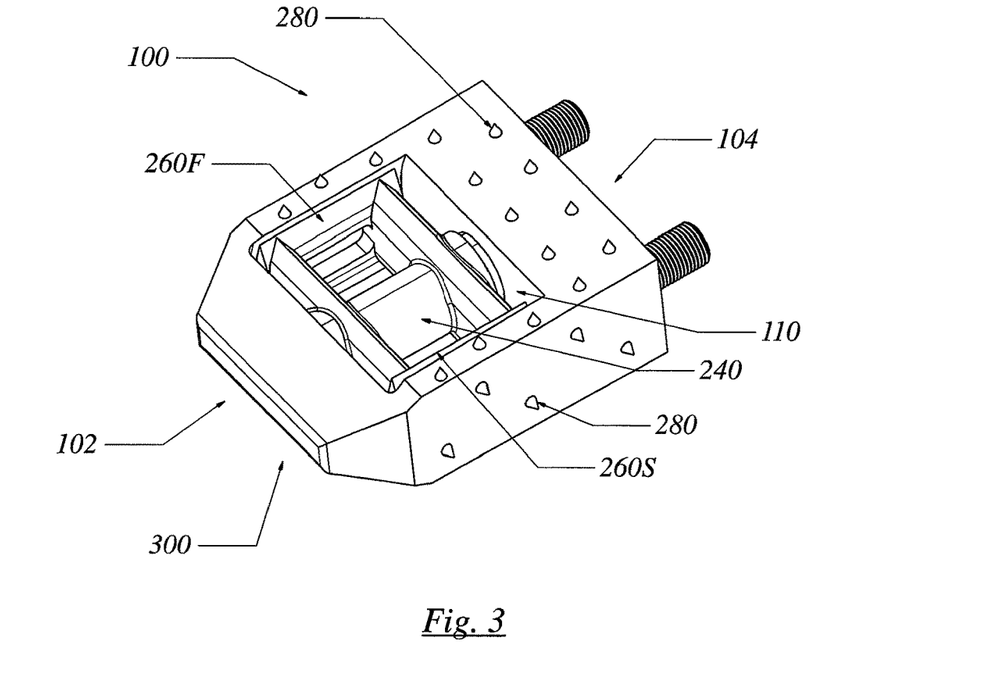
FIG. 3 is a perspective of a preferred embodiment of implant (100) that includes barbs.

FIG. 3 is a perspective of a preferred embodiment of implant (100) that includes barbs (280).

Figure 4:
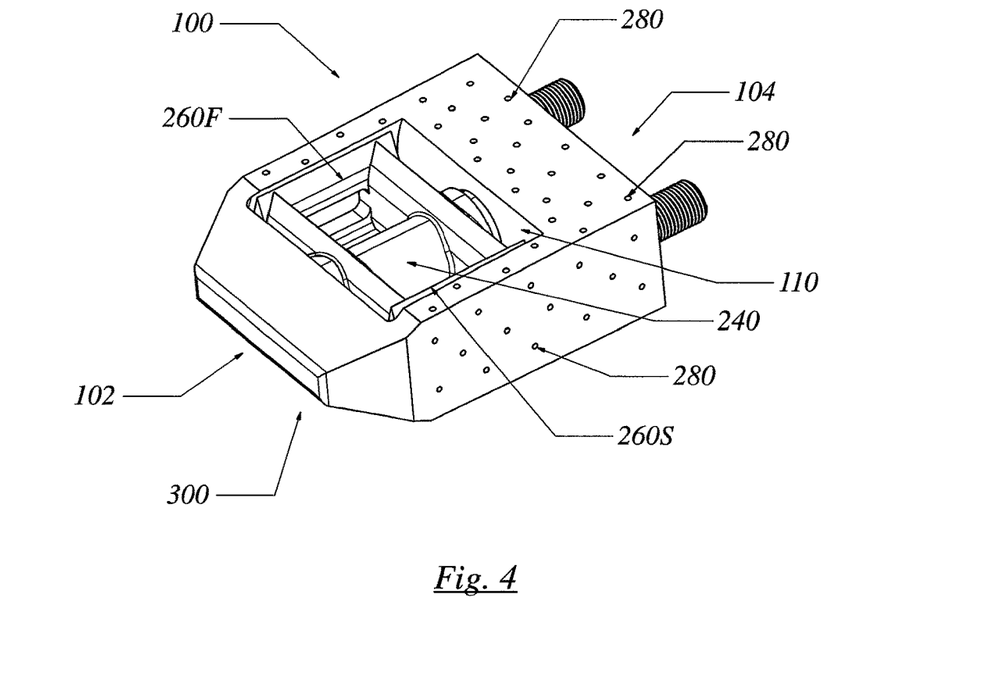
FIG. 4 is a perspective of a preferred embodiment of implant (100) that includes surface treatments.

FIG. 4 is a perspective of a preferred embodiment of implant (100) that includes surface treatments (280).

Within the scope of the current invention, surface treatments (280) can include barbs, micropores or metal or abrasive particles incorporated into or onto the biocompatible composition.

Figure 5:
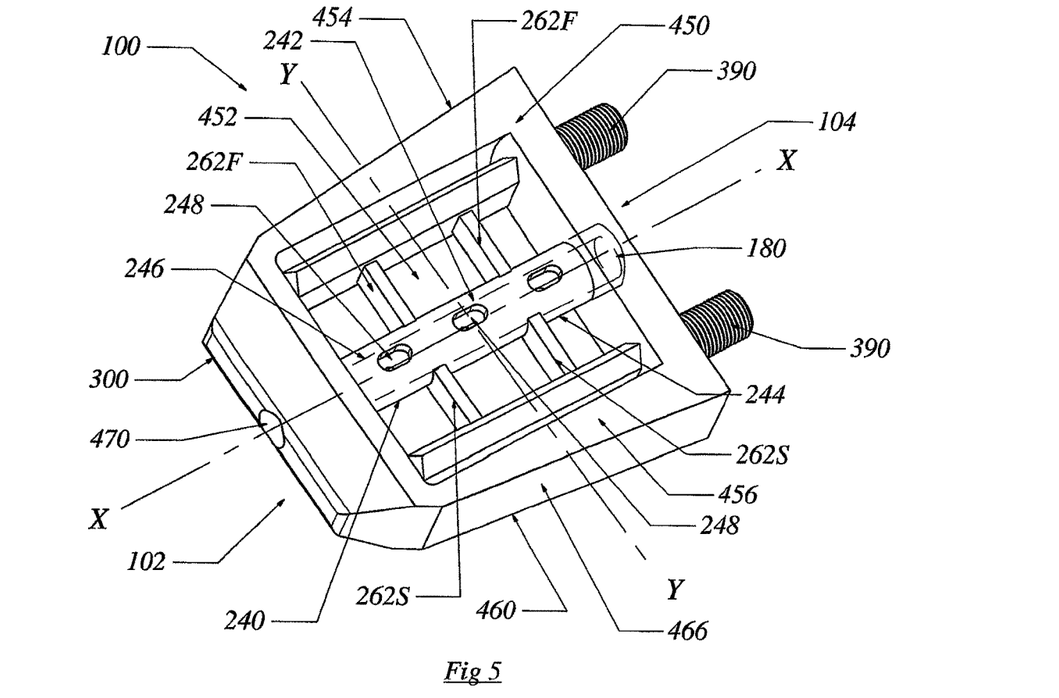
FIG. 5 is a perspective of another preferred embodiment of joint implant (100).
Figure 6:
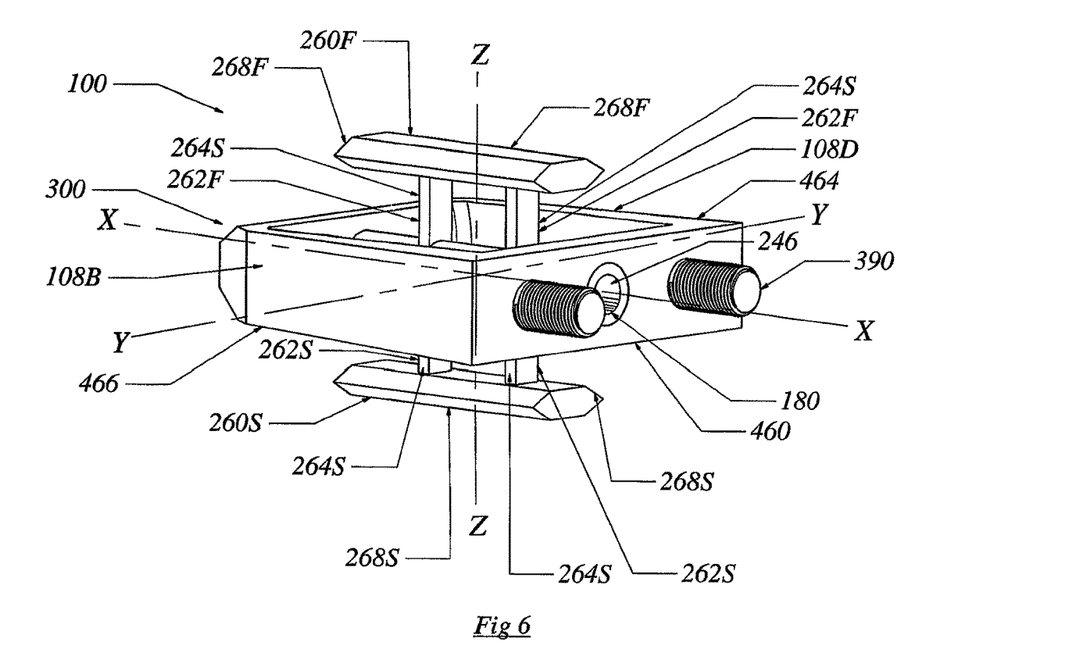
FIG. 6 is a perspective of another preferred embodiment of joint implant (100).

With reference to FIGS. 5 and 6, a preferred embodiment of implant (100) is enabled. Implant (100) is provided with a biocompatible construction including a longitudinal axis X-X that can be measured in a coexisting or parallel direction of a longest dimension of the biocompatible construction. In selected preferred embodiments, when engineering parameters require, longitudinal axis X-X can be offset from center.

Implant (100) is provided with first trapezoidal surface (450) and opposed trapezoidal surface (460). First trapezoidal surface (450) includes aperture (452) and two margins (454, 456) of equal length. Second trapezoidal surface (460) includes aperture (462) and two margins (464, 466) of equal length. Implant (100) also includes anterior side (102), posterior or surgeon facing side (104) and lateral sides (108B, 108D) extending between anterior side (102) and surgeon facing side (104). Anterior side (102) and surgeon facing side (104) extend between first trapezoidal surface (450) and second trapezoidal surface (460). Anterior side (102) of implant (100) is provided with cutting edge (300) on the outward face of anterior side (102).

Orifice (470) extends through cutting edge (300) and anterior side (102). Among other things, orifice (470) allows access of a guide wire (not shown in FIGS. 5-6) when medically required. Other preferred embodiments of the current invention do not include orifice (470). Surgeon facing side (104) is provided with a bearing (180) and at least one connector (390) adapted to engage an insertion device (not shown in FIGS. 5 and 6).

As shown, rotatable shaft (240) extends along longitudinal axis X-X from orifice (470) into bearing (180). However, in other preferred embodiments, rotatable shaft (240) can contact bearing (180) and extend through bearing (180).

Rotatable shaft (240) includes conduit (242) extending through the length of shaft (240). Conduit (242) is defined by the inward face (246) of shaft's (240) cylindrical wall (244). One or more windows (248) are positioned in cylindrical wall (240). Each window (248) is adapted to expose conduit (242) the surgical created cavity external from joint implant (100). Conduit (242) can carry one or more substances that diffuse through windows (248) into the surround surgically created cavity (not shown in FIGS. 5 and 6).

Arms (262F, 262S) are connected to rotatable shaft (240) and support cutters (260F, 260S). Blades (268F, 268S) associated with cutters (260F, 260S) are adapted to cut when rotated in a clockwise or counterclockwise direction when shaft (240) is rotated. Sharp edges (264F, 264S) of arms (262F, 262S) can be adapted to remove cartilage, expose subcortical bone and/or morselize graft material. Tool (360) as shown in FIG. 2 can be used to rotate shaft (240). In select preferred embodiments anterior side (102) is of lesser cross-sectional area than surgeon facing side (104).

With a view toward to FIGS. 5 and 6 and within the scope of the current invention, preferred embodiments of joint implant (100) can have a length greater than a width. In select preferred embodiments, the width of joint implant (100) is greater than the height of joint implant (100). In other preferred embodiments of joint implant (100), the height of implant (100) is greater than the width of joint implant (100). The inward sides of anterior side (102), posterior side (104) and margins (454, 456, 464, 466) facing longitudinal axis X-X create an available inner volume of implant (100) which can receive osteogenic as well as other substances.

As measured along longitudinal axis X-X of implant's (100) biocompatible construction, preferred embodiments are provided with cutting edge (300) that can be up to about 3 millimeters in length. The length of implant (100), including cutting edge (300) can be from about 6 millimeters to about 50 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

With respect to this application and in view FIGS. 5 and 6, the longitudinal axis of joint implant (100) is measured along axis X-X. Axis X-X can correspond with shaft (240) or in some preferred embodiments, shaft (240) can be offset from axis X-X. Width of implant (100) is measured along axis Y-Y or an axis parallel to axis Y-Y shown in FIGS. 5 and 6. Height of joint implant is measured along axis Z-Z or an axis parallel to axis Z-Z of the joint implant's biocompatible construction.

Figure 7:
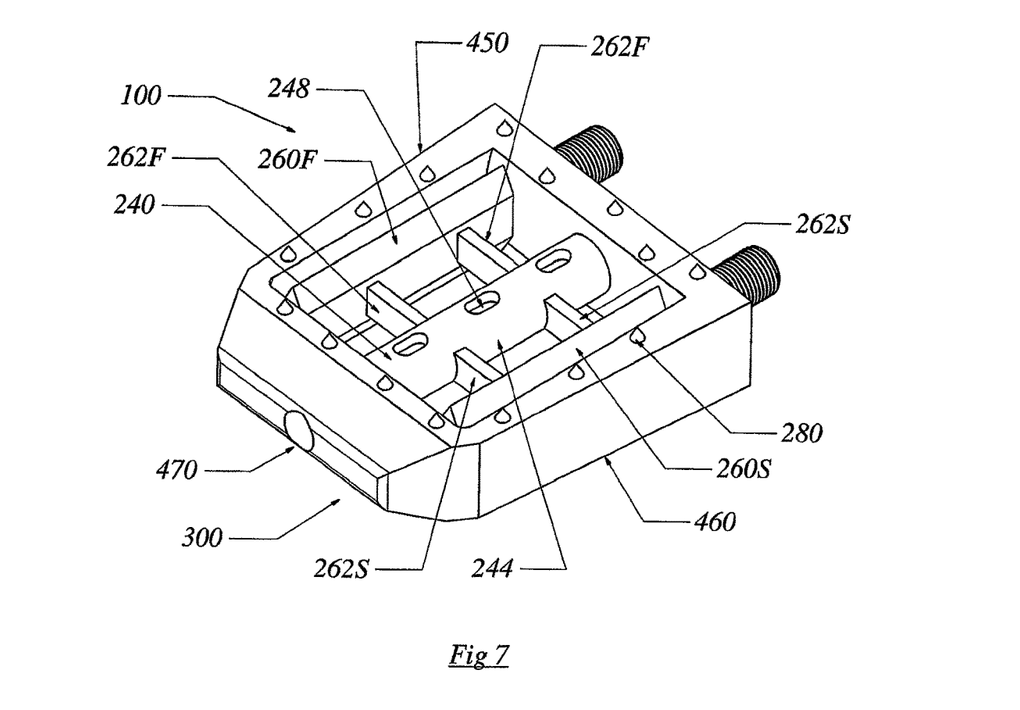
FIG. 7 is a perspective of another preferred embodiment of joint implant (100) that includes surface treatments.

FIG. 7 is a perspective of a preferred embodiment of implant (100) that includes barbs (280).

Figure 8:
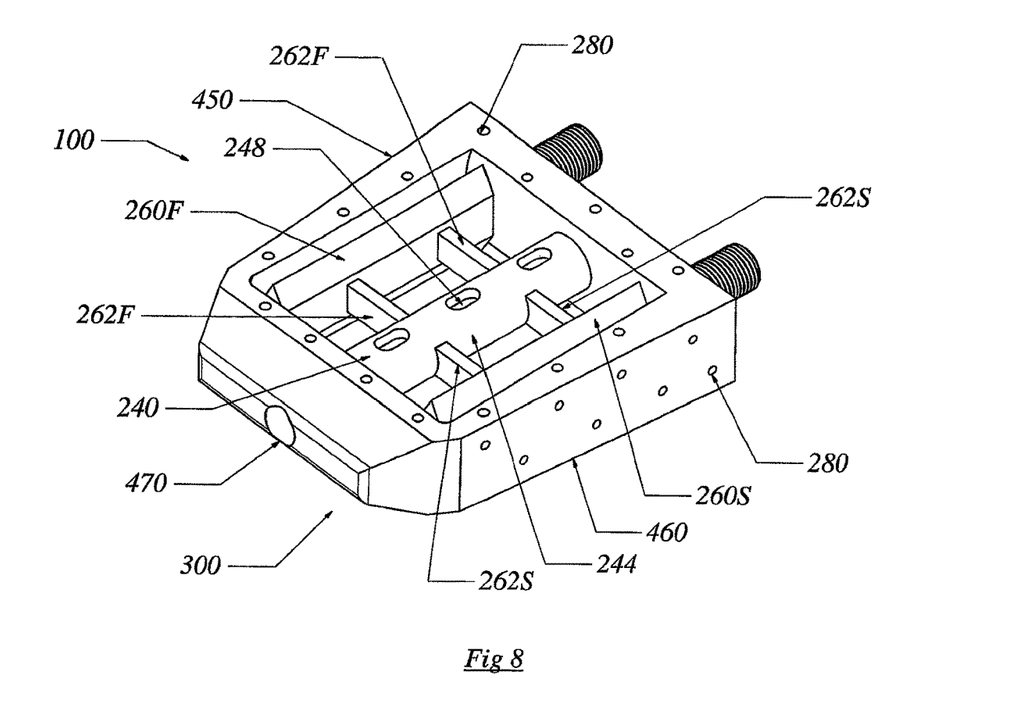
FIG. 8 is a perspective of another preferred embodiment of joint implant (100) that includes surface treatments.

FIG. 8 is a perspective of a preferred embodiment of implant (100) that includes surface treatments (280).

As previously indicated, within the scope of the current invention, surface treatments (280) can include barbs, micropores or metal or abrasive particles incorporated into or onto the biocompatible composition.

Select preferred embodiments of the current invention have been disclosed and enabled as required by Title 35 of the United States Code and/or the Articles of the Patent Cooperation Treaty.

What is claimed is:

1. A joint implant comprising a biocompatible construction with a longitudinal axis extending in a coexisting or parallel direction of a longest dimension of the biocompatible construction; the biocompatible construction comprising:
   a) upper and lower surfaces each comprising an opening therein outward from the longitudinal axis;
   b) an anterior side perpendicular to the longitudinal axis comprising:
   i) an outward cutting edge traversing a length of the anterior side; and
   ii) an inward socket not extending through the anterior side;
   c) a surgeon facing side, opposite the anterior side, comprising a bearing defining a pathway therethrough and opposed first and second gaps extending through the surgeon facing side;
   d) a rotatable shaft engaging the socket and extending along the longitudinal axis from the socket through the bearing, wherein the rotatable shaft is detachable from the socket and the bearing; and
   e) first and second arms connected with the rotatable shaft and extending outwardly therefrom; the first and second arms supporting first and second cutters, respectively, the first and second cutter each comprising a blade, wherein on rotation of the rotatable shaft, each blade is adapted to cut in a clockwise or counterclockwise direction.

2. The joint implant of claim 1, the biocompatible construction further comprising first and second lateral sides connected with the anterior side and the surgeon facing side, wherein the biocompatible construction includes a length greater than a width.

3. The joint implant of claim 2, wherein:
   a) a diameter of the rotatable shaft diameter engaging the socket is less than a diameter of the shaft proximate the bearing; and
   b) the biocompatible construction's anterior side has a lesser cross-sectional area than a cross-sectional area of the surgeon facing side.

4. The joint implant of claim 3, comprising one or more connectors connected to the surgeon facing side, wherein each connector is adapted to engage a device.

5. The joint implant of claim 4, wherein:
   a) the first and second arms comprise one or more sharp edges adapted to remove cartilage, expose subcortical bone and/or morselize graft material; and
   b) one or more surfaces of the biocompatible construction comprise surface treatments.

6. A joint implant comprising a biocompatible construction with a longitudinal axis spanning a longest dimension of the biocompatible construction; the biocompatible construction comprising:
   a) upper and lower surfaces each comprising an opening therein outward from the longitudinal axis;
   b) an anterior side perpendicular to the longitudinal axis comprising:
   i) an outward cutting edge traversing a length of the anterior side; and
   ii) a blind inward socket;
   c) a surgeon facing side comprising a bearing and first and second gaps; the bearing and the first and second gaps together creating a continuous ingress/egress pathway extending through the surgeon facing side;
   d) a rotatable shaft, extending along or parallel to the longitudinal axis, engaging the socket and the bearing, wherein the rotatable shaft is detachable from the biocompatible construction; and
   e) first and second arms connected with the rotatable shaft and extending outwardly therefrom; the first and second arms supporting first and second cutters, respectively, the first and second cutter each comprising a blade, wherein on rotation of the rotatable shaft, each blade is adapted to cut in a clockwise or counterclockwise direction.

7. The joint implant of claim 6, the biocompatible construction further comprising first and second lateral sides connected with the anterior side and the surgeon facing side, wherein the biocompatible construction includes a length greater than a width.

8. The joint implant of claim 7, wherein:
   a) a diameter of the rotatable shaft engaging the socket is less than a diameter of the rotatable shaft proximate the bearing; and
   b)
   the biocompatible construction's anterior side has a lesser cross-sectional area than a cross-sectional area of the surgeon facing side.

9. The joint implant of claim 8, comprising one or more connectors connected to the surgeon facing side, wherein each connector is adapted to engage a device.

10. The joint implant of claim 9, wherein:
  a) the first and second arms comprise one or more sharp edges adapted to remove cartilage, expose subcortical bone and/or morselize graft material; and
  b) one or more surfaces of the biocompatible construction comprise surface treatments.

11. A joint implant comprising a biocompatible construction with a longitudinal axis spanning a longer dimension of the biocompatible construction; the biocompatible construction comprising:
  a) upper and lower trapezoidal surfaces each comprising an opening therein outward from the longitudinal axis;
  b) an anterior side perpendicular to the longitudinal axis comprising:
    i) an outward cutting edge traversing a length of the anterior side; and
    ii) a blind inward socket;
  c) a surgeon facing side comprising a bearing;
  d) a rotatable shaft, extending along the longitudinal axis, engaging the socket and the bearing, wherein the rotatable shaft is detachable from the biocompatible construction through a continuous bidirectional ingress/egress pathway defined through the bearing of the surgeon facing side; and
  e) first and second arms connected with the rotatable shaft and extending outwardly therefrom; the first and second arms supporting first and second cutters, respectively, the first and second cutters each comprising a blade, wherein on rotation of the rotatable shaft, each blade is adapted to cut in a clockwise or counterclockwise direction.

12. The joint implant of claim 11, wherein the biocompatible construction further comprises first and second gaps adjacent the bearing creating a pathway for detaching the rotatable shaft from the biocompatible construction.

13. The joint implant of claim 12, the biocompatible construction further comprising first and second lateral sides connected with the anterior side and the surgeon facing side, wherein the biocompatible construction includes a length greater than a width.

14. The joint implant of claim 13, wherein:
  a) a diameter of the rotatable shaft engaging the socket is less than a diameter of the rotatable shaft proximate the bearing;
  b) the first and second gaps are perpendicular to the longitudinal axis; and
  c) the biocompatible construction's anterior side has a lesser cross-sectional area than a cross-sectional area of the surgeon facing side.

15. The joint implant of claim 14, comprising one or more connectors connected to the surgeon facing side, wherein each connector is adapted to engage a device.

16. The joint implant of claim 15, wherein:
  a) the first and second arms each comprise one or more sharp edges adapted to remove cartilage, expose subcortical bone and/or morselize graft material; and
  b) one or more surfaces of the biocompatible construction comprise surface treatments.

17. A joint implant comprising a biocompatible construction with a longitudinal axis spanning a longer dimension of the biocompatible construction; the biocompatible construction comprising:
  a) a first trapezoidal surface comprising a first aperture therein and a first two margins of equal length;
  b) a second trapezoidal surface opposed from the first trapezoidal surface; the second trapezoidal surface comprising a second aperture therein and a second two margins of equal length;
  c) an anterior side perpendicular to the longitudinal axis extending between the first and second trapezoidal surfaces; the anterior side comprising a cutting edge traversing a length of the anterior side and an orifice extending through the anterior side and the cutting edge;
  d) a surgeon facing side comprising a bearing defining a pathway therethrouqh; the surgeon facing side extending between the first and second trapezoidal surfaces; and
  e) a rotatable shaft extending from the orifice into the bearing; the rotatable shaft comprising:
    i) a conduit extending through an entire length of the rotatable shaft; the conduit defined by an inward face of the rotatable shaft's cylindrical wall, wherein the conduit is configured to be in fluid communication with a surgically created cavity external from the conduit;
    ii) one or more windows, positioned in the cylindrical wall; each window exposing the conduit to the surgically created cavity external from the conduit; and
    iii) first and second arms connected with the rotatable shaft and extending outwardly therefrom; the first and second arms supporting first and second cutters, respectively, the first and second cutters each comprising a blade, wherein on rotation of the rotatable shaft, each blade is adapted to cut in a clockwise or counterclockwise direction.

18. The joint implant of claim 17, comprising one or more connectors connected to the surgeon facing side, wherein each connector is adapted to engage a device.

19. The joint implant of claim 18, wherein one or more surfaces of the biocompatible construction comprise surface treatments.

20. The joint implant of claim 19, wherein the first and second arms comprise one or more sharp edges adapted to remove cartilage, expose subcortical bone and/or morselize graft material.

21. A joint implant comprising a biocompatible construction with a longitudinal axis spanning a longer dimension of the biocompatible construction; the biocompatible construction comprising:
  a) upper and lower trapezoidal surfaces each comprising an opening therein outward from the longitudinal axis;
  b) an anterior side perpendicular to the longitudinal axis comprising a cutting edge traversing a length of the anterior side and an orifice extending through the anterior side;
  c) a surgeon facing side comprising a bearing defining a pathway therethrough, wherein the anterior side has a lesser cross-sectional area than a cross-sectional area of the surgeon facing side; and
  d) a rotatable shaft extending from the orifice into the bearing; the rotatable shaft comprising:
    i) a conduit extending through an entire length of the rotatable shaft; the conduit defined by an inward face of the rotatable shaft's cylindrical wall, wherein the conduit is configured to be in fluid communication with a surgically created cavity external from the conduit;
    ii) one or more windows, positioned in the cylindrical wall; each window exposing the conduit to the surgically created cavity external from the conduit; and
    iii) first and second arms connected with the rotatable shaft and extending outwardly therefrom; the first and second arms supporting first and second cutters, respectively, the first and second cutters each comprising a blade, wherein on rotation of the rotatable shaft, each blade is adapted to cut in a clockwise or counterclockwise direction.

22. The joint implant of claim 21, wherein the biocompatible construction further includes a length greater than a width.

23. The joint implant of claim 22, comprising one or more connectors connected to the surgeon facing side, wherein each connector is adapted to engage a device.

24. The joint implant of claim 23, wherein one or more surfaces of the biocompatible construction comprise surface treatments.

25. The joint implant of claim 24, wherein the first and second arms comprise one or more sharp edges adapted to remove cartilage, expose subcortical bone and/or morselize graft material.

* * * * *